United States Patent

Hernandez et al.

[11] Patent Number: 5,855,209
[45] Date of Patent: Jan. 5, 1999

[54] PATIENT'S HAND IMMOBILIZER

[76] Inventors: Lisa Hernandez, 32390 IH-10 West;
Joseph R. Kabanek, 32390 IH-10 West, both of Boerne, Tex. 78006

[21] Appl. No.: 880,761

[22] Filed: Jun. 23, 1997

[51] Int. Cl.[6] .................................................... A61F 5/37
[52] U.S. Cl. ............................................ 128/878; 128/879
[58] Field of Search ................................. 128/845, 846, 128/877, 878, 879; 602/5, 20, 21, 22; 2/16, 21, 160

[56] References Cited

U.S. PATENT DOCUMENTS

| | | | |
|---|---|---|---|
| 1,867,258 | 7/1932 | Fruehauf | 602/22 |
| 2,863,449 | 12/1958 | Spencer | 602/21 |
| 5,113,849 | 5/1992 | Kuiken | 602/21 |
| 5,282,483 | 2/1994 | Wang | 128/882 |
| 5,560,375 | 10/1996 | Kabanek | 128/878 |

*Primary Examiner*—Michael A. Brown
*Attorney, Agent, or Firm*—Paul H. Gallagher

[57] ABSTRACT

A main panel of aluminum shaped to the hand, with side tab segments for bending over the wrist and the main part of the hand and over the ends of the fingers. It includes layers of sponge material glued to both of opposite faces of the aluminum layer.

6 Claims, 2 Drawing Sheets

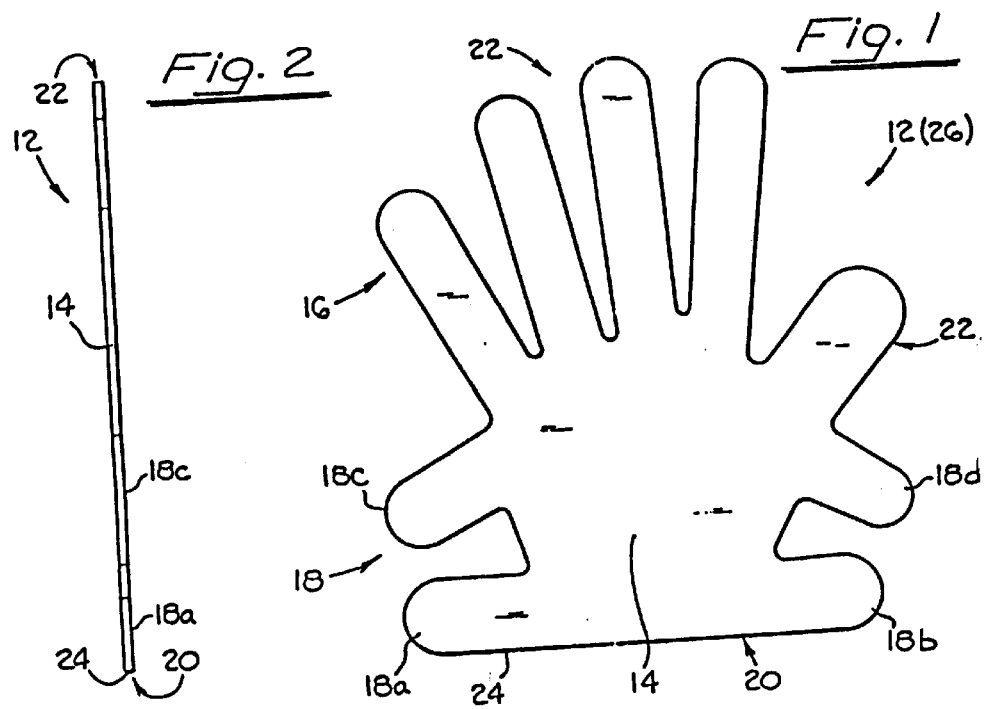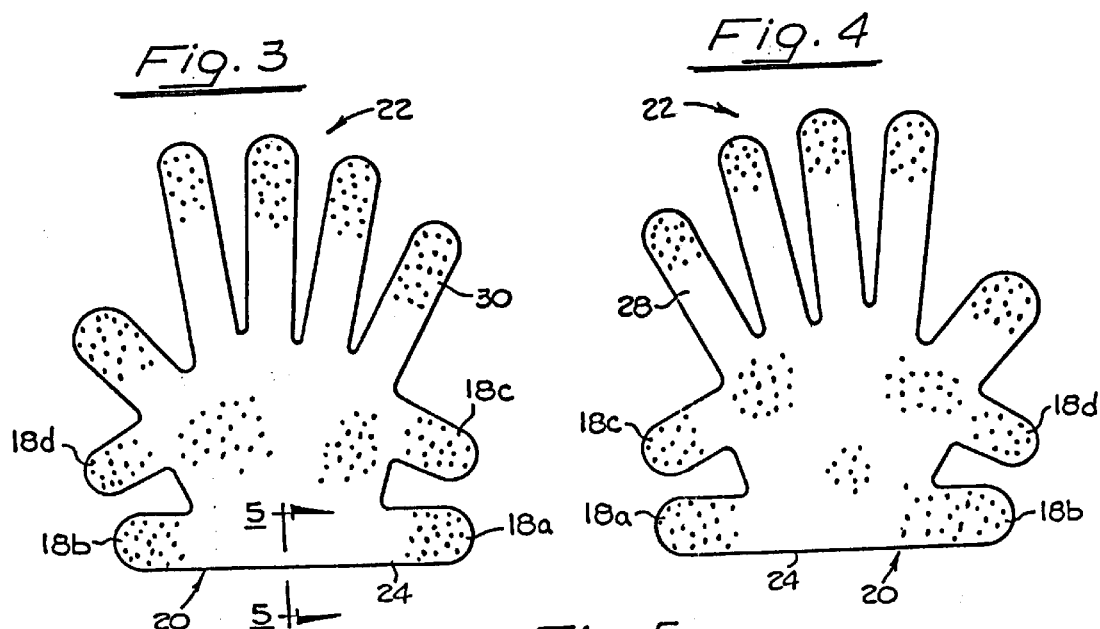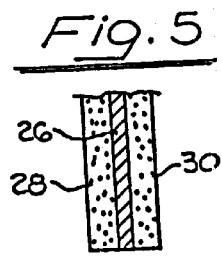

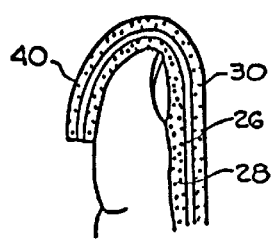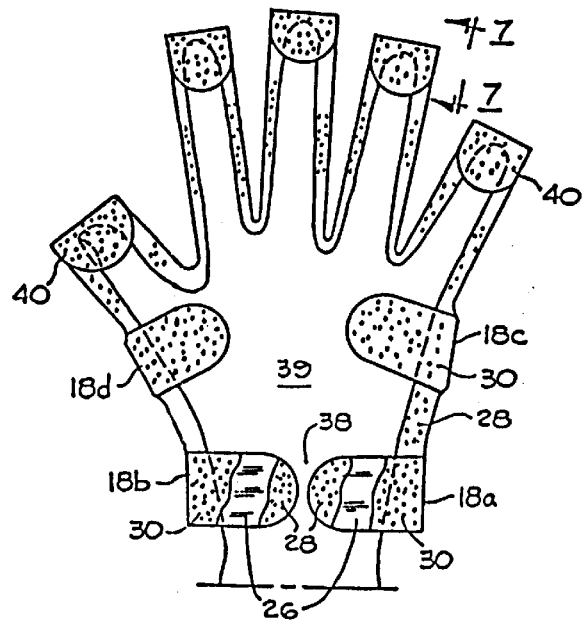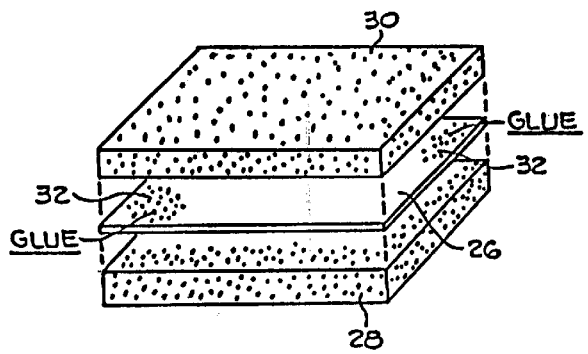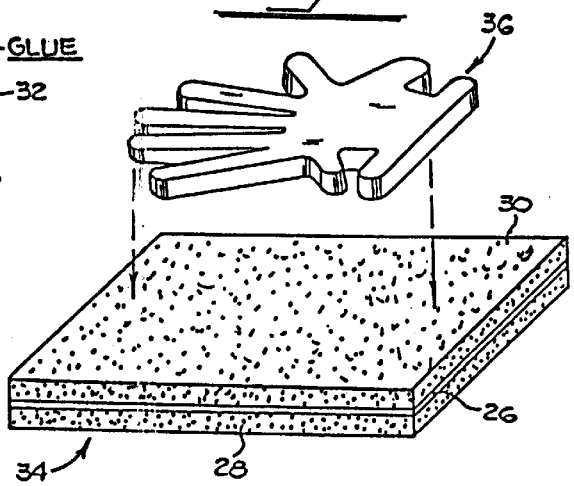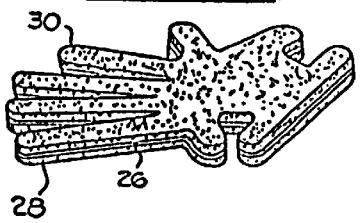

PATIENT'S HAND IMMOBILIZER

SUMMARY OF THE INVENTION

The invention relates generally to an aluminum immobilizer and constitutes an improvement over our invention covered by U.S. Pat. No. 5,560,375, dated Oct. 1, 1996.

The device includes an aluminum layer or panel which forms the structural basis of the article, that layer possessing the desired features characteristic of aluminum, as brought out in our prior patent mentioned, e.g. as contrasted to lead. The aluminum provides the necessary mechanical structure, and corresponding strength, for holding the patient's hand in outstretched flat position, and it includes peripheral tabs or elements for bending over onto corresponding elements of the hand for holding it on the hand.

It is desired that a cushion layer be secured to the aluminum layer to provide comfort to the patient, this cushion layer being between the aluminum layer and surface of the hand. Thus the cushion layer is applied on the front or "inside" surface of the aluminum layer, being thus oriented according to the manner in which the article is applied to the hand. Heretofore, and basically, the cushion layer is for the purpose stated, namely providing comfort, and does not essentially enter into the strength of the article.

The aluminum layer, and thereby the final product, is symmetrical, in that it can be applied either to the right hand or left hand, and thus it assumes inner and outer surfaces according to which hand it is applied. In the use of the device, it is desired of course that the source of their use, i.e. clinic, doctor's office, be supplied with a quantity of the articles, and ordinarily there may the same number of right hands as left hands, or approximately so, involved in a successive treatments. However, it does happen that such numbers are not equal, and the articles ready for use may be depleted in one situation or the other. This is of course an annoyance, and even a difficulty, even though, such as in an emergency, the article may be reversed with the aluminum panel directly engaging the surface of the hand, and secured in position similarly to securing it to the proper hand.

To overcome the foregoing difficulty, the immobilizer of the present invention is provided with cushion layers on both of opposite flat sides of the basic aluminum layer, to render it of ambidextrous character, so that any single one article can be applied to either the right or left hand with equal effectiveness. Therefore a user can keep a large number of the devices on hand, all of the same kind so as not to require him to estimate the proportion of right and left hands to be treated, and have the assurance that the supply will accommodate all hands to be treated.

Therefore an overall and broad object is the provision of a device that can be of such character, selectively, as an ambidextrous article for use on either hand, or with a single cushion layer (as in our prior patent referred to), or even in an extreme or emergency case, without any cushion layer.

BRIEF DESCRIPTION OF THE INDIVIDUAL FIGURES OF THE DRAWINGS

FIG. 1 is a face view of the basic aluminum layer of the immobilizer.

FIG. 2 is an edge view of the panel shown in FIG. 1.

FIG. 3 is a view of the article, on a smaller scale oriented according to FIG. 1, and showing a cushion panel on the front face surface of the aluminum panel.

FIG. 4 is a view similar to FIG. 3, showing the opposite side of the article.

FIG. 5 is a sectional view taken at line 5—5 of FIG. 3.

FIG. 6 is a face view of the patient's hand with the immobilizer applied thereto.

FIG. 7 is a view taken at line 7—7 of FIG. 6.

FIG. 8 is a perspective view of sheets of aluminum and cushion material, in aggregate form, and indicating a step in the method of forming the final article.

FIG. 9 is a view of the layers of FIG. 8 fitted together, and a cutter for cutting through the combination of the layers to form the final article.

FIG. 10 is a perspective view at an angle, from the side, of the finished article.

DETAILED DESCRIPTION OF THE DRAWINGS

Attention is directed first to FIGS. 1 and 2 which show the basic structural part of the device. This part, identified 12 is an aluminum layer, to which the other layers of cushion material are applied. This aluminum layer is made from a simple flat sheet of aggregate material, formed as referred to below, in the shape of a hand having extremities corresponding to the fingers, and other terminal elements forming tabs for securing the immobilizer to the hand.

For convenience, and simplicity in referring to the immobilizer, it may be referred to as an article, or device. The cushion layers that are applied to the aluminum layer are described hereinbelow, and the entire article is formed by applying aggregate sheets of aluminum and cushion material together and then cutting the article therefrom.

Referring to the overall shape of the device, reference is made to FIG. 1 showing the aluminum layer 12 which has the shape of the finished article. This layer has a main segment 14 corresponding to the main part of the hand, or metacarpus; it also includes digital segments 16 corresponding to the fingers of the hand, and side segments 18 forming tabs to be identified in detail hereinbelow.

For purposes of identification and clarification, the elements of the patient's body concerned herein are: the limb, which includes the full arm, including the full hand; the arm, which extends down to and includes the wrist; the hand, which is the portion outwardly of the wrist; all of the fingers together are identified as digits, but those fingers other than the thumb may also be referred to as fingers, to distinguish them from the thumb. The device has an inner end 20 and an outer end 22.

The side tabs 18 include a first pair 18a, 18b, extending laterally outward at the rear end of the article, these tabs and the remainder of the article together having a common straight transverse border line 24 at the inner end of the device; the side tabs also include a second pair 18c, 18d, extending generally outwardly, forwardly of the tabs 18a, 18b although at a different angle. The side tabs 18c, 18d may extend generally perpendicularly from the adjacent digital segments 16.

Our prior patent identified above, discloses a main aluminum layer and a single cushion or sponge layer, and each the main aluminum layer, and the cushion layer, is formed from a flat, plain sheet of aggregate material. In the present case there are two such cushion layers, and correspondingly they are formed from a pair of flat, plain sheets of aggregate material. This arrangement is represented particularly in FIGS. 8 and 9.

FIG. 8 shows a sheet 26 of aggregate aluminum material, and two sheets 28, 30 of cushion or sponge material, in aggregate form. These latter two cushion sheets are disposed on opposite sides of the main sheet 26 and secured together in face-to-face relation as shown in FIG. 9. This securement may be done a suitable glue indicated at 32, and the three sheets, all of the same outline size, thus form a multi-layer, composite sheet 34.

FIG. 9 includes a cutter 36 of the size and shape of the intended article, being in the form of a "cooker cutter". The cutter cuts through the composite article, i.e. the two layers of sponge material and the aluminum material. In this method of forming the article, a great advantage results in producing an accurate fitting together of the ultimate three layers, and the ease in doing so, in addition to presenting a trim experience.

The aluminum layer is of relatively great strength, so that forces such as those tending to double-up the hand, will not deflect the side tabs. While the dimension of the aluminum layer may be any within a substantial range, it is found that a thickness of. 0.034" is satisfactory. The sponge layers may be for example of 7/32" in thickness. As will be obvious, these dimensions are not limiting, but indicative.

The article is applied to the patient's hand as represented in FIGS. 6 and 7. When so applied, the tabs 18 are bent up and over the corresponding elements of the limb. The innermost segments 18a, 18b, are positioned adjacent the wrist of the patient and are therefore folded over the wrist.

The hand of the patient assumes a larger transverse dimension, outwardly of the wrist, as indicated at 38, just inwardly of the thumb. The tabs 18a, 18b are positioned inwardly from the large portion, and thus they snugly hold the article from moving or sliding off the hand, in outward direction.

The other pair of tabs, 18c, 18d are positioned at the main part of the hand 39, and are bent up and over that main part, these tabs thereby holding the article against sideways movement.

The article is of sufficient size that when it is applied to the hand, the ends of the digits of the hand, do not reach out to the ends of those tabs, and the tabs are then bent over the ends of the digits of the hand, as shown in FIGS. 6 and 7. These end portions are identified 40 and hold the article on the hand relative to the ends of the fingers.

The flat surfaces of the opposite sides of the article, as viewed face-on are symmetrical, i.e. they represent and are shaped to the respective hands, i.e. either the right or the left. Although an article made up of an aluminum layer and a single cushion layer is satisfactory for a particular hand, as disclosed in our prior patent identified above, there would have to be in stock enough of a particular kind to accommodate a predetermined number of hands of the same handedness, i.e. right handed or left handed, throughout a series of treatments of hands. However, such supply of articles having a single cushion layer may not coincide with the number of hands to be treated, although there may be other articles of the opposite handedness. The ambidextrous nature of the article of the present invention overcomes that contingency, in that a single article or immobilizer can be applied to either the right or the left hand, with equal effectiveness. In the latter case where there are two layers of cushion material, there would of course always be a cushion on the outer surface, after the article is applied to the hand, but this is not objectionable, and does not interfere with treatment of the hand. The great advantage is that a given quantity of articles would accommodate a corresponding number of hands for treatment, regardless whether they are right hands or left hands. The article is identical on both sides, except for outline shape, in that a layer of sponge material may be exposed, or the bare surface of the aluminum may be exposed.

Notwithstanding the foregoing features and advantages, it is nevertheless possible, to apply an article made up of a single aluminum layer, without cushion layers, to hold the hand immobilized, in the unusual event that articles with cushion layers are not accessible. Therefore the scope of the invention includes (a) a single layer of only aluminum, (b) having a sponge layer on either side but on only one side, or (c) sponge layers on both sides.

We claim:

1. An article constituted by a patient's hand immobilizer, the hand constituting the terminal portion of the limb, of the patient comprising, a rigid layer to be fitted to the hand and having an inner end and an outer end, the layer being integral and of one-piece of aluminum, and being planar in shape, and of uniform thickness throughout its outline dimensions, the layer including a) a main segment shaped to the metacarpus, b) digital segments shaped to the fingers respectively and positioned correspondingly thereto, and c) a first pair and a second pair of side tabs, said side tabs extending laterally outwardly from the main segment of the article, the first pair of side tabs being at the extreme inner end of the article and thereby inwardly of the position of the widest part of the hand and adjacent the wrist, the second pair of side tabs being forwardly of the first pair and adjacent the forward end of the main segment, the article being made of same material on opposite side surfaces and the digital segments and the side tabs having free outer end portions bendable over the corresponding portions of the hand operable for securing the article on the hand.

2. An article according to claim 1 and including, a layer of sponge material of the same size and shape as the aluminum layer secured to each of the opposite flat sides of the latter, whereby the article can be applied to either the right hand or the left side with equal effectiveness in that in either case a layer of sponge material is applied directly to and engages the hand.

3. An article according to claim 1 wherein, the aluminum layer constitutes the entire article.

4. A method of making a patient's hand immobilizer, having various elements dimensioned and shaped according to corresponding elements on the hand, comprising, providing a sheet of aggregate aluminum material, and a pair of sheets of aggregate sponge material, all larger than the intended immobilizer, and each and all continuous and uniform in character and thickness throughout their outline dimensions, securing the sheets together by adhesion with the sheet of aluminum between the sheets of sponge material, throughout their interengaging areas, thereby forming a compound article which is consequently of aggregate character, and cutting from that compound article a piece which forms the immobilizer, and solely constitutes the entire immobilizer.

5. An article constituted by a patient's hand immobilizer, the hand constituting the terminal portion of the limb of the patient, comprising, a rigid layer to be fitted to the hand and having an inner end and an outer end, the layer being integral and of one-piece of aluminum, and being planar in shape, and of uniform thickness throughout its outline dimensions, the layer including, a) a main segment shaped to the metacarpus, b) digital segments shaped to the fingers respectively positioned correspondingly thereto, and the article being made of the same material on opposite side surfaces, and the digital segments having free outer end portions bendable over the ends of the fingers of the hand operable for securing the article on the hand.

6. An article according to claim 5 wherein, the layer includes a pair of side tabs extending outwardly from the main segment of the article, and the side tabs have free outer end portions bendable over the corresponding portions of the limb operable for securing the article on the hand.

* * * * *